United States Patent
Okuda et al.

(10) Patent No.: US 10,447,015 B2
(45) Date of Patent: Oct. 15, 2019

(54) SPARK PLUG PRODUCTION METHOD, SPARK PLUG PRODUCTION DEVICE AND ASSEMBLY INSPECTION METHOD

(71) Applicant: NGK SPARK PLUG CO., LTD., Nagoya-shi, Aichi (JP)

(72) Inventors: Masafumi Okuda, Nagoya (JP); Toshiyuki Otsuki, Komaki (JP); Kanako Nishiyama, Kasugai (JP)

(73) Assignee: NGK SPARK PLUG CO., LTD., Nagoya-shi (JP)

( * ) Notice: Subject to any disclaimer, the term of this patent is extended or adjusted under 35 U.S.C. 154(b) by 0 days.

(21) Appl. No.: 16/290,374

(22) Filed: Mar. 1, 2019

(65) Prior Publication Data

US 2019/0199070 A1 Jun. 27, 2019

Related U.S. Application Data

(62) Division of application No. 15/557,847, filed as application No. PCT/JP2016/001550 on Mar. 17, 2016, now Pat. No. 10,270,229.

(30) Foreign Application Priority Data

Mar. 18, 2015 (JP) .................. 2015-054097

(51) Int. Cl.
*H01T 21/02* (2006.01)
*H01T 21/00* (2006.01)
(Continued)

(52) U.S. Cl.
CPC .............. *H01T 13/60* (2013.01); *F02P 17/12* (2013.01); *H01T 21/02* (2013.01); *G01N 27/205* (2013.01); *H01T 13/36* (2013.01)

(58) Field of Classification Search
CPC ................................ H01T 21/02; H01T 21/00
(Continued)

(56) References Cited

U.S. PATENT DOCUMENTS 2,175,038 A 10/1939 Soper
2,603,685 A 7/1952 Bychinsky
(Continued)

FOREIGN PATENT DOCUMENTS

CN 102983502 A 3/2013
JP 2004-108817 A 4/2004
(Continued)

OTHER PUBLICATIONS

International Search Report from corresponding International Patent Application No. PCT/JP2016/001550 dated Jun. 7, 2016.
(Continued)

*Primary Examiner* — Christopher M Raabe
(74) *Attorney, Agent, or Firm* — Kusner & Jaffe

(57) ABSTRACT

A method of producing a spark plug comprises (a) a step of combining a metallic shell and an insulator; (b) a step of inserting a portion of the assembly on its forward end side into a pressure container; (c) a step of bringing an insulating member into contact with the outer circumferential surface of a base side portion of the insulator over the entire circumference thereof, and pressing the assembly so as to close the opening by the assembly; and (d) a step of pressurizing the interior of the pressure container and applying a predetermined voltage between the terminal electrode and the metallic shell.

7 Claims, 9 Drawing Sheets

(51) Int. Cl.
*H01T 13/60* (2011.01)
*F02P 17/12* (2006.01)
*G01N 27/20* (2006.01)
*H01T 13/36* (2006.01)

(58) Field of Classification Search
USPC .......................................................... 445/67
See application file for complete search history.

(56) References Cited

U.S. PATENT DOCUMENTS

| | | |
|---|---|---|
| 4,570,124 A | 2/1986 | Fuchs |
| 2004/0051537 A1 | 3/2004 | Hori |
| 2012/0001532 A1* | 1/2012 | Kure ................. H01T 21/02 313/118 |
| 2014/0065915 A1 | 3/2014 | Kyuno et al. |
| 2014/0111213 A1 | 4/2014 | Cunningham et al. |
| 2014/0141679 A1 | 5/2014 | Kyuno |
| 2014/0141680 A1 | 5/2014 | Kyuno |
| 2016/0223604 A1 | 8/2016 | Hirose et al. |
| 2018/0069379 A1 | 3/2018 | Okuda et al. |

FOREIGN PATENT DOCUMENTS

| | | |
|---|---|---|
| JP | 2004-335140 A | 11/2004 |
| JP | 2005-251485 A | 9/2005 |
| JP | 2007-134132 A | 5/2007 |
| JP | 2013-089428 A | 5/2013 |
| JP | 2014-083627 A | 5/2014 |
| JP | 2014-130805 A | 7/2014 |

OTHER PUBLICATIONS

Extended European Search Report issued in corresponding European Patent Application No. 16764500.1 dated Oct. 2, 2018.
U.S. Appl. No. 15/557,847, filed Sep. 13, 2017.

* cited by examiner

SPARK PLUG PRODUCTION METHOD, SPARK PLUG PRODUCTION DEVICE AND ASSEMBLY INSPECTION METHOD

RELATED APPLICATIONS

This application is a division of U.S. application Ser. No. 15/557,847, filed Sep. 13, 2017 (now U.S. Pat. No. 10,270,229, issued Apr. 23, 2019), which is a National Stage of International Application No. PCT/JP2016/001550 filed Mar. 17, 2016, which claims the benefit of Japanese Patent Application No. 2015-054097, filed Mar. 18, 2015, the entire contents of which are incorporated herein by reference.

FIELD OF THE INVENTION

The present invention relates to production and inspection of a spark plug.

BACKGROUND OF THE INVENTION

An example of a spark plug conventionally used for an internal combustion engine is a spark plug in which spark discharge is produced in a gap (spark discharge gap) between a columnar center electrode and a bent ground electrode. In such a spark plug, a ceramic insulator is disposed between the center electrode and a metallic shell on which the ground electrode is provided. If the ceramic insulator has a defect such as a pinhole, discharge may occur through the defect, and a through hole may be formed in the ceramic insulator to extend in the thickness direction thereof. If such a through hole is formed, there arises a possibility of failure to produce normal spark discharge. In view of the foregoing, during a process of manufacturing a spark plug, there has been performed a step (hereinafter referred to as a withstanding voltage test step) of applying a high voltage between an electrode (e.g., a center electrode) disposed in an axial hole of a ceramic insulator and an electrode (e.g., a metallic shell) disposed outside the ceramic insulator and determining whether or not the ceramic insulator has a defect, on the basis of a voltage waveform measured at that time or an image captured at that time. In the withstanding voltage test step of Patent Document 1, the entire ceramic insulator is disposed in a closed container, and a high voltage is applied between the electrode disposed in the axial hole of the ceramic insulator and the electrode disposed outside the axial hole in a state in which the interior of the closed container is pressurized.

However, in the spark plug production method of Japanese Patent Application Laid-Open (kokai) No. 2007-134132, since the entire ceramic insulator is disposed in the container, the container must have a very large volume. Therefore, a long time is needed to pressurize and depressurize the interior of the container, and a long time is needed to dispose the ceramic insulator into the container and remove it from the container. Therefore, there have been a problem of requiring a longer time to produce the spark plug and a problem of lower production efficiency. In addition, since the container for accommodating the ceramic insulator is large in size, there has been a problem that the size of the entire production device increases. Also, since the surface area of the container is large, there has been a problem that a material of high rigidity must be used as the material of the container in order to allow the container to have a sufficient degree of robustness such that the container can withstand the application of pressure of, for example, about 2 MPa (mega pascal), and therefore, the container has a very large weight. Further, since it is necessary to provide a lock mechanism or a like mechanism at an opening of the closed container through which the ceramic insulator is disposed in the container and removed therefrom, and to provide means for supplying electric power to the interior of the closed container, there has been a problem that production cost increases.

Further, in the spark plug production method of Japanese Patent Application Laid-Open (kokai) No. 2007-134132, the ceramic insulator solely undergoes the withstanding voltage test, and the ceramic insulator is not tested in a state in which the ceramic insulator is actually used; i.e., in the form of an assembly in which the ceramic insulator is combined with a metallic shell. Therefore, there has been a problem of failing to meet the market's need to produce a spark plug while performing the withstanding voltage test in the configuration in which the insulator is actually used.

The present invention has been accomplished to address the above-described problem. The present invention can be realized as the following modes or application examples.

SUMMARY OF THE INVENTION (1) According to one aspect of the present invention, there is provided a spark plug production method comprised of: (a) a step of combining a tubular metallic shell and an insulator such that the metallic shell covers an outer circumferential surface of a forward end side of the insulator so as to obtain an assembly, the metallic shell having a ground electrode at its forward end portion, the insulator having an axial hole and holding a terminal electrode in the axial hole such that a portion of the terminal electrode on its base end side is exposed from the axial hole; (b) a step of inserting a portion of the assembly on its forward end side into a pressure container through an opening of the pressure container; (c) a step of bringing an insulating member into contact with an outer circumferential surface of a base end side of the insulator over the entire circumference of the base end side in a state in which an axial line of the assembly and an axial line of the opening coincide with each other, and pressing the assembly so as to close the opening by the assembly; and (d) a step of pressurizing an interior of the pressure container and applying a predetermined voltage between the terminal electrode and the metallic shell, wherein the step (b) includes a step of inserting the portion of the assembly on the forward end side into the pressure container such that a gap formed between an outer circumferential surface of the insulator and an inner circumferential surface of the metallic shell on the forward end side of the assembly is disposed in the pressure container.

According to the spark plug production method of this mode, only a portion of the assembly on the forward end side is inserted into the pressure container. Therefore, attachment of the assembly to the pressure container and removal of the assembly from the pressure container can be performed within a short period of time. Also, since only a portion of the assembly is inserted into the pressure container, the volume of the pressure container can be decreased, whereby the time required to pressurize the interior of the pressure container in the step (d) can be shortened. As a result, the time required for production of the spark plug can be shortened, and a decrease in production efficiency can be suppressed. In addition, since the volume of the pressure container can be decreased, the space required for production of the spark plug can be reduced. Also, the insertion into the pressure container and the application of the predetermined voltage are performed for the assembly obtained by combining the metallic shell and the insulator. Therefore, the spark plug can be produced while the application of the predetermined voltage, etc. are performed for a member in a configuration closer to a configuration in which the insulator is actually used, as compared with the case where the insertion into the pressure container and the application of the predetermined voltage are performed for the insulator alone.

(2) In accordance with a second aspect of the present invention, there is provided a spark plug production method as described above, wherein the step (c) may include a step of bringing the assembly into close contact with the pressure container in the direction of the axial line of the assembly through a seal provided around the opening. According to the spark plug production method of this mode, the assembly comes into close contact with the pressure container in the direction of the axial line through the seal. Therefore, the gas tightness of the pressure container can be improved. As a result, the pressure within the pressure container can be increased, whereby application of higher voltage between the terminal electrode and the metallic shell can be realized. Also, it is possible to prevent the assembly from being damaged by the pressure container when the assembly is pressed.

(3) In accordance with a third aspect of the present invention, there is provided a spark plug production method as described above, further comprised of: (e) a step of photographing or observing the terminal electrode and the metallic shell applied with the predetermined voltage from a position on the pressure container opposite the opening. According to the spark plug production method of this mode, a forward end side of the assembly applied with the predetermined voltage is photographed or observed. Therefore, the determination as to whether or not the insulator has a defect can be easily performed through utilization of an image captured by the photographing or the result of the observation.

(4) In accordance with a fourth aspect of the present invention, there is provided a spark plug production method as described above, wherein the step (c) may include a step of bringing an electrically conductive member into contact with a base end portion of the terminal electrode, the electrically conductive member being used for applying the predetermined voltage. According to the spark plug production method of this mode, the electrically conductive member is brought into contact with the terminal electrode in a state in which the axial line of the assembly and the axial line of the opening coincide with each other. Therefore, it is possible to prevent the electrically conductive member from coming into contact with the terminal electrode in a misaligned condition.

(5) In accordance with a fifth aspect of the present invention, there is provided a spark plug production method as described above, wherein the step (c) may include a step of pressing the metallic shell, along the axial line of the assembly, in a direction from a base end toward a forward end of the assembly to thereby close the opening by the assembly. According to the spark plug production method of this mode, the metallic shell is pressed, along the axial line of the assembly, in the direction from the base end toward the forward end of the assembly. Therefore, the pressure application axis and the axis of the opening (the close contact axis) can be rendered coincident with each other. As a result, it is possible to prevent the assembly from closing the opening in a misaligned condition, to thereby improve the gas tightness of the interior of the pressure container.

Also, the configuration for pressing can be simplified as compared with a configuration in which these axes do not coincide with each other. Namely, in the configuration in which the pressure application axis and the close contact axis deviate from each other, a member for transmitting force between these axes becomes necessary. In addition, when the interior of the pressure container is pressurized in the step (d), a large force must be applied to the assembly along the direction of the close contact axis so as to prevent the assembly from coming off the pressure container due to the pressurization. In order to transmit such a large force from the pressure application axis, it is necessary to prepare a member of high rigidity as a member for transmitting force between the axes. This results in an increase in the size of a production apparatus and an increase in cost. In contrast, in the production method of the above-described mode, since the member for transmitting force between the axes is unnecessary, it is possible to reduce the size of the production apparatus and reduce cost.

(6) In accordance with a sixth aspect of the present invention, there is provided a spark plug production method, further comprised of: (f) a step of, after the step (d), displacing at least one of the electrically conductive member and the insulating member such that the insulating member relatively moves, along the axial line of the assembly, in relation to the insulator in a direction from a forward end toward a base end of the assembly. According to the spark plug production method of this mode, the insulating member which is in close contact with the insulator can be easily disengaged from the insulator.

(7) In accordance with a seventh aspect of the present invention, there is provided a spark plug production method as described above, wherein the step (f) may be performed by causing the electrically conductive member to press the terminal electrode, along the axial line of the assembly, in the direction from the base end toward the forward end of the assembly and displacing the insulating member in the direction from the forward end toward the base end of the assembly. According to the spark plug production method of this mode, it is unnecessary to engage the assembly and the pressure container with each other for detachment of the insulating member. Therefore, a complicated step (e.g., a step of bringing the metallic shell of the assembly into screw engagement with the pressure container) is unnecessary when a portion of the assembly on the forward end side is inserted into the pressure container. Therefore, the time required to insert the assembly into the pressure container and remove the assembly from the pressure container be shortened, whereby the time required to produce the spark plug can be shortened. Also, it is possible to prevent the assembly from being damaged when the assembly is inserted into the pressure container and removed from the pressure container.

(8) In accordance with an eighth aspect of the present invention, there is provided a spark plug production method as described above, wherein the step (c) may include a step of fitting the insulating member onto the terminal electrode from a base end side of the terminal electrode and pressing the insulating member, along the axial line of the assembly, toward the forward end side of the assembly, to thereby bring the insulating member into close contact with at least either of an outer circumferential surface of the terminal electrode and an outer circumferential surface of a base end side of the insulator. According to the spark plug production method of this mode, the insulating member is brought into close contact with the assembly by pressing the insulating member toward the forward end side of the assembly along the axial line of the assembly. Therefore, the insulating member can be brought into close contact with the insulator uniformly in the circumferential direction. As a result, it is possible prevent generation of discharge (flashover) which is generated between the metallic terminal and the metallic shell such that the discharge creeps along the surface of the insulator.

(9) In accordance with a ninth aspect of the present invention, there is provided a spark plug production method as described above, wherein the step (d) may include a step of bringing an earthing electrode into contact with the metallic shell on a base end side of the assembly in relation to a seat surface of the metallic shell, the seat surface closing the opening and maintaining a gas tightness of the pressure container. According to the spark plug production method of this mode, the configuration of the pressure chamber can be simplified as compared with a configuration in which the metallic shell and the earthing electrode are brought into contact with each other within the pressure container. Also, the time required to bring the earthing electrode into contact with the metallic shell can be shortened.

(10) In accordance with a tenth aspect of the present invention, there is provided a spark plug production method as described above, wherein the insulator may hold a center electrode in a forward end side of the axial hole such that a portion of the center electrode on its forward end side is exposed from the axial hole; and the method may further comprise (g) a step of, after the step (d), bending the ground electrode toward the forward end portion of the center electrode. According to the spark plug production method of this mode, the step of bending the ground electrode is performed after the step (d). Therefore, in the step (d), the distance between the ground electrode and the center electrode can be made relatively long. As a result, the voltage applied to the assembly can be made higher.

(11) In accordance with an eleventh aspect of the present invention, there is provided a spark plug production method as described above, further comprised of: (h) a step of, after the step (d), disposing a gasket on the metallic shell at a position located forward of and adjacent to a seat surface of the metallic shell along the axial line of the assembly, the seat surface closing the opening and maintaining a gas tightness of the pressure container. According to the spark plug production method of this mode, the gasket is disposed on the assembly after the step (d). Therefore, unlike the case where the gasket is disposed on the assembly before the step (d), it is possible to prevent deterioration of the gasket, which deterioration would otherwise occur as a result of performance of the step (c).

(12) In accordance with a twelfth aspect of the present invention, there is provided a spark plug production method as described above, wherein the pressure container may include the opening as a sole opening; and the step (b) may include a step of inserting forward-end-side portions of a plurality of the assemblies different from each other into a plurality of the pressure containers. According to the spark plug production method of this mode, only a portion of a single assembly on the forward end side is inserted into the pressure container. Therefore, the size of the pressure container can be reduced. Also, it is possible to produce a plurality of spark plugs simultaneously while shortening the production time per spark plug.

(13) In accordance with a thirteenth aspect of the present invention, there is provided a spark plug production method as described above, further comprised of: (i) a step of bringing an earthing electrode into contact with the metallic shell, wherein the step (c) may include a step of bringing an electrically conductive member into contact with a base end portion of the terminal electrode, the electrically conductive member being used for applying the predetermined voltage, and wherein at least one of the earthing electrode and the electrically conductive member may be chamfered. According to the spark plug production method of this mode, at least one of the earthing electrode and the electrically conductive member is chamfered. Therefore, it is possible to prevent occurrence of flashover starting from an edge of the electrically conductive member or the earthing electrode.

The present invention can be realized in various modes other than the spark plug production method. For example, the present invention can be realized as a spark plug testing method, a spark plug testing apparatus, a method of testing an insulator for a spark plug, an apparatus for testing an insulator for a spark plug, and a spark plug.

DETAILED DESCRIPTION OF THE PREFERRED EMBODIMENTS

A. Embodiment

Figure 1:
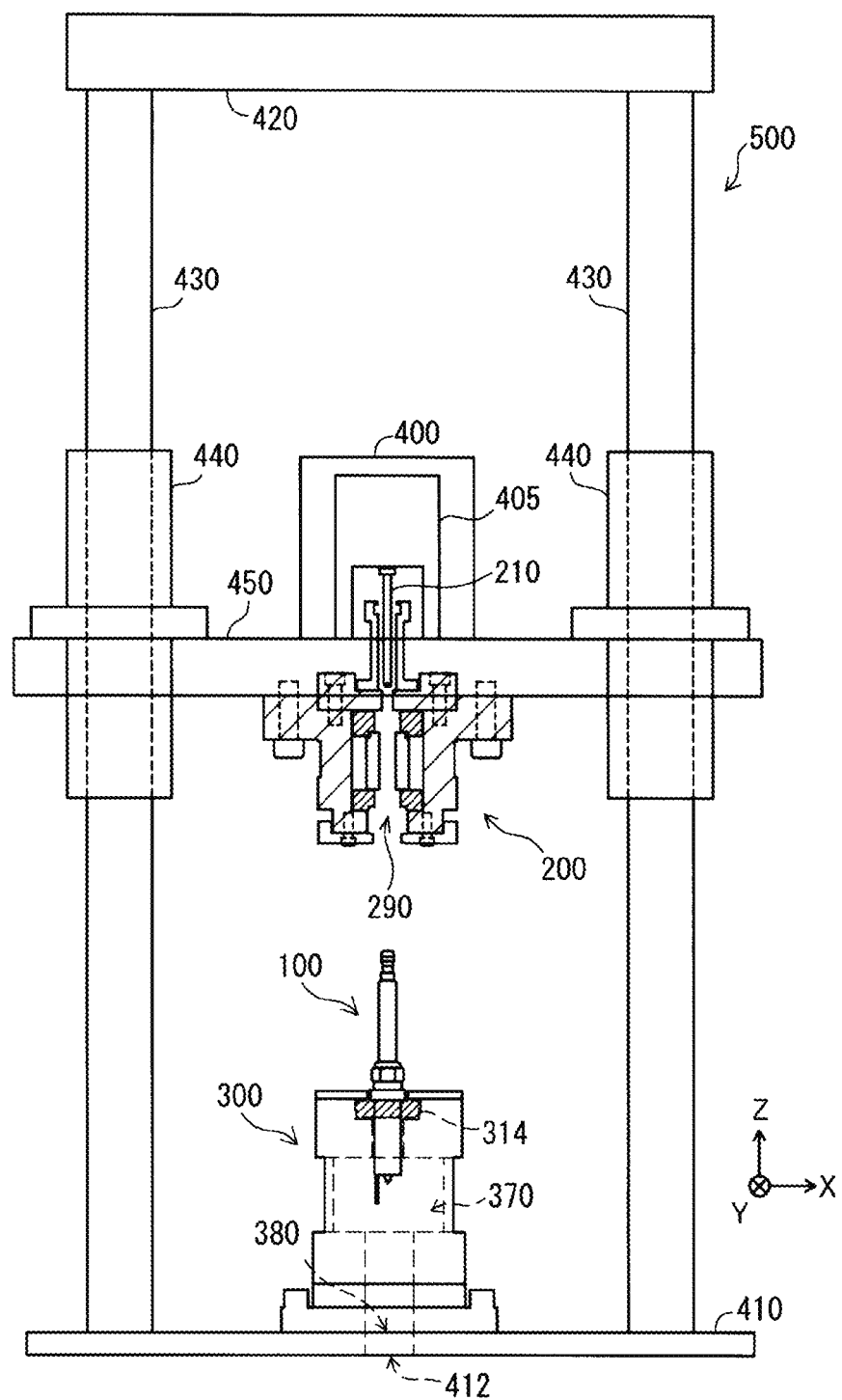
FIG. 1 is a plan view showing the overall structure of a spark plug production device which is one embodiment of the present invention.

A1. Overall Structure of a Spark Plug Production Device:

FIG. 1 is a plan view showing the overall structure of a spark plug production device which is one embodiment of the present invention. The spark plug production device 500 is an apparatus for producing spark plugs and is used to carry out some steps of a spark plug production method which will be described later. Notably, in FIG. 1, a +Z direction shows the vertically upper side, and an X-Y plane shows a horizontal plane.

The spark plug production device 500 includes a pressing and energizing section 200, a pressure container 300, a voltage application section 400, a lower fixed plate 410, an upper fixed plate 420, two supporting columns 430, two slide supports 440, and a moving shelf 450.

The pressing and energizing section 200 presses an assembly 100 set onto the pressure container 300 vertically downward, to thereby seal the interior of the pressure container 300 with the assembly 100. Also, the pressing and energizing section 200 supplies electricity to the assembly 100 when a withstanding voltage test is performed during production of spark plugs which will be described later. The pressing and energizing section 200 is fixed to the surface of the moving shelf 450 on the vertically lower side thereof. The assembly 100 is a member which is produced in a spark plug production process, and becomes a completed spark plug through predetermined steps (a ground electrode bending step and a gasket attaching step which will be described later). The pressing and energizing section 200 has an insertion hole 290 formed in a center portion thereof and extending in the Z-axis direction. When the withstanding voltage test is performed during the production of spark plugs which will be described later, a portion of the assembly 100 on the base end side is accommodated in the insertion hole 290. In the present embodiment, the term "base end side" means a side where an end portion on the +Z direction side is present, and the term "forward end side" means a side where an end portion on the −Z direction side is present. The pressing and energizing section 200 includes an electrically conductive pin 210 provided on the base end side. The electrically conductive pin 210 is disposed to be movable within the insertion hole 290 along the Z-axis direction. Notably, the electrically conductive pin 210 corresponds to the electrically conductive member in the claims. The specific structures of the pressing and energizing section 200 and the assembly 100 will be described later.

The pressure container 300 has a center axis extending along the Z-axis direction, has an approximately cylindrical external shape, and is fixed to the surface of the lower fixed plate on the vertically upper side thereof. An approximately cylindrical space (hereinafter referred to as the "chamber 370") with a bottom is formed inside the pressure container 300. A seal 314 having an opening formed at the center is disposed at the end of the chamber 370 on the base end side. The opening of the seal 314 is closed by the assembly 100, whereby the interior of the chamber 370 becomes gastight. The interior of the chamber 370 is connected to an unillustrated air pump, and the pressure within the chamber 370 is adjusted by the air pump. In the present embodiment, the interior of the chamber 370 is pressurized to 5 MPa (mega pascal). Notably, the interior of the chamber 370 may be pressurized, not to 5 MPa, but to an arbitrary pressure within the range of 0.5 MPa to 5 MPa. A window is provided in a bottom portion 380 of the chamber 370 for visual observation of the interior of the chamber 370. The window is formed of, for example, a transparent acrylic material or a glass material. The specific structure of the pressure container 300 will be described later.

The voltage application section 400 applies a high voltage to the assembly 100 when the withstanding voltage test is performed in the spark plug production method which will be described later. The voltage application section 400 includes a conductive pin drive section 405. The conductive pin drive section 405 moves the electrically conductive pin 210 along the Z-axis direction by pushing and pulling the electrically conductive pin 210 along the Z-axis direction. Also, the conductive pin drive section 405 applies a voltage to the electrically conductive pin 210 such that the electrically conductive pin 210 has a predetermined potential.

The lower fixed plate 410 is a plate-shaped member disposed parallel to the X-Y plane and has a through hole 412 formed in an approximately center portion thereof and extending in the thickness direction (the Z-axis direction). The through hole 412 faces the bottom portion 380 of the pressure container 300. Therefore, from the vertically lower side of the lower fixed plate 410, the interior of the chamber 370 can be viewed through the through hole 412 and the bottom portion 380. Notably, an unillustrated image capturing device is disposed in the through hole 412, and a forward end portion of the assembly 100 disposed in the chamber 370 is photographed. The upper fixed plate 420 is a plate-shaped member disposed parallel to the X-Y plane and is disposed above the lower fixed plate 410 such that the upper fixed plate 420 is vertically spaced from the lower fixed plate 410 by a predetermined distance. Each of the two supporting columns 430 is a circular columnar member extending along the Z-axis direction, and is connected at one end to the lower fixed plate 410 and connected at the other end to the upper fixed plate 420. The two slide supports 440 each have an approximately cylindrical external shape and are slidably attached to the respective supporting columns 430. The two slide supports 440 are connected to opposite end portions of the moving shelf 450 located on the +X direction side and the −X direction side, respectively. The positions of the two slide supports 440 in the Z-axis direction coincide with each other. When the slide supports 440 slide, the moving shelf 450 moves upward or downward while maintaining the state parallel to the X-Y plane. The two slide supports 440 are driven upward and downward by an unillustrated drive section. The moving shelf 450 is a plate-shaped member disposed parallel to the X-Y plane. The pressing and energizing section 200 is disposed on the surface of the moving shelf 450 on the vertically lower side thereof, and the voltage application section 400 is disposed on the surface of the moving shelf 450 on the vertically upper side thereof. Notably, the moving shelf 450 has a through hole formed in an approximately center portion thereof and extending in the thickness direction (the Z-axis direction), and a portion of the pressing and energizing section 200 is disposed in the through hole. In the present embodiment, each of the lower fixed plate 410, the upper fixed plate 420, the two supporting columns 430, the two slide supports 440, and the moving shelf 450 is formed of steel.

Figure 2:
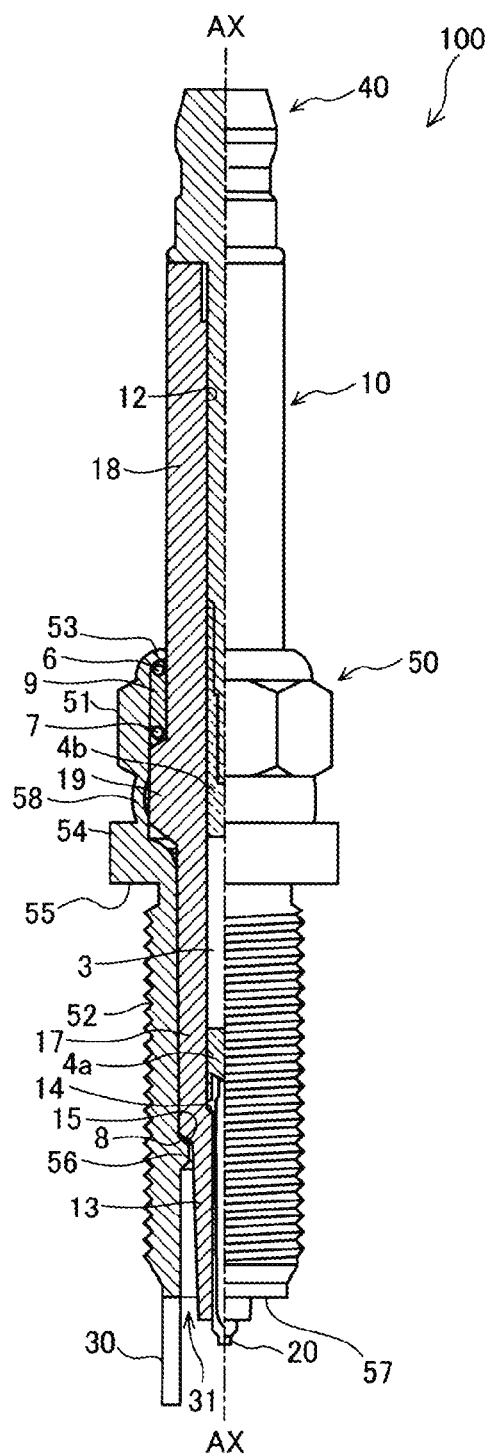
FIG. 2 is a partial sectional view showing the specific structure of an assembly 100 shown in FIG. 1.

A2. Specific Structure of the Assembly 100:

FIG. 2 is a partial sectional view showing the specific structure of the assembly 100 shown in FIG. 1. The assembly 100 extends along an axial line AX indicated by an alternate long and short dash line in FIG. 2 and has a slender columnar external shape. An external front view of the assembly 100 is shown on the right side of the axial line AX, and a cross-sectional view of the assembly 100 cut along a cross section passing through the axial line AX is shown on the left side of the axial line AX. In the following description, the lower side of FIG. 2 (in the direction parallel to the axial line AX) will be referred to as the forward end side and the upper side of FIG. 2 will be referred to as the base end side.

The assembly 100 includes a ceramic insulator 10, a center electrode 20, a ground electrode 30, a metallic terminal 40, and a metallic shell 50. The center electrode 20 has a rod-like external shape and is disposed in an axial hole 12 of the ceramic insulator 10 such that its forward end projects from the ceramic insulator 10. The center electrode 20 and a ceramic resistor 3 are disposed in the axial hole 12 of the ceramic insulator 10 such that a seal 4a is sandwiched between the base end portion of the center electrode 20 and the ceramic resistor 3. Also, a seal 4b is disposed such that the seal 4b is in contact with the base end of the ceramic resistor 3. Also, a forward end portion of the metallic terminal 40 is disposed inside the axial hole 12 of the ceramic insulator 10 such that the forward end portion is in contact with the seal 4b. A base end portion of the metallic terminal 40 protrudes from an end portion of the ceramic insulator 10 on the base end side. The center electrode 20 is electrically connected to the metallic terminal 40 through the ceramic resistor 3 and the seals 4a and 4b. The outer circumference of the ceramic insulator 10 is held by the metallic shell 50 at a position which is separated from the metallic terminal 40 toward the forward end side. The ground electrode 30 has a rod-like external shape, is joined to the forward end surface 57 of the metallic shell 50, and is disposed parallel to the axial line AX. During the spark plug production process, the ground electrode 30 is bent toward the center electrode 20 so that a spark discharge gap which is a gap for generating spark is formed between the ground electrode 30 and the forward end of the center electrode 20.

The ceramic insulator 10 is an insulating member formed by firing a ceramic material such as alumina. The ceramic insulator 10 has a tubular external shape and has at its center the axial hole 12 for accommodating the center electrode 20 and the metallic terminal 40. The ceramic insulator 10 has a center trunk portion 19 formed at the center in the axial direction and having a large outer diameter. A base-end-side trunk portion 18 for insulating the metallic terminal 40 and the metallic shell 50 from each other is formed on the metallic terminal 40 side of the center trunk portion 19. A forward-end-side trunk portion 17 which is smaller in outer diameter than the base-end-side trunk portion 18 is formed on the center electrode 20 side to the center trunk portion 19. A leg portion 13 is formed on the forward end side of the forward-end-side trunk portion 17. The leg portion 13 is smaller in outer diameter than the forward-end-side trunk portion 17 and is tapered such that its outer diameter decreases toward the center electrode 20. Notably, the ceramic insulator 10 corresponds to the insulator in the claims.

The metallic shell 50 is a cylindrical metallic member which surrounds and holds a portion of the ceramic insulator 10, the portion extending from a forward-end-side portion of the base-end-side trunk portion 18 to the leg portion 13. In the present embodiment, the metallic shell 50 is formed of low carbon steel and is entirely plated with nickel, zinc, or the like. The metallic shell 50 has a tool engagement portion 51, an attachment screw portion 52, and a seal portion 54. A tool for attaching the spark plug to an engine head is engaged with the tool engagement portion 51 of the metallic shell 50. The attachment screw portion 52 of the metallic shell 50 has a screw thread which comes into screw-engagement with an attachment threaded hole of the engine head. The seal portion 54 of the metallic shell 50 is located at the root of the attachment screw portion 52 and has a flange-like external shape. In the spark plug production process, a gasket is attached to the forward end surface 55 of the seal portion 54. The gasket is pressed against the engine head by the seal portion 54, whereby the gas tightness of the interior of an engine chamber is secured. Notably, the forward end surface 55 corresponds to the seat surface in the claims. The forward end surface 57 of the metallic shell 50 has a circular annular shape. The leg portion 13 of the ceramic insulator 10 projects from the center of the forward end surface 57, and the center electrode 20 projects from the forward end surface of the leg portion 13. A gap 31 having a predetermined dimension is formed between the inner circumferential surface of the axial hole of the metallic shell 50 and the outer circumferential surface of the leg portion 13 of the ceramic insulator 10.

The metallic shell 50 has a thin-walled crimp portion 53 formed on the base end side of the tool engagement portion 51. Also, a compressively deformable portion 58 which is also thin-walled like the crimp portion 53 is provided between the seal portion 54 and the tool engagement portion 51. Annular ring members 6 and 7 are disposed between the outer circumferential surface of the base-end-side trunk portion 18 and the inner circumferential surface of the metallic shell 50 extending from the tool engagement portion 51 to the crimp portion 53, and powder of talc 9 is charged between the two ring members 6 and 7. In the spark plug production process, the crimp portion 53 is pressed toward the forward end side while being bent inward, whereby the compressively deformable portion 58 is compressed and deformed. As a result of the compressive deformation of the compressively deformable portion 58, within the metallic shell 50, the ceramic insulator 10 is pressed toward the forward end side through the ring members 6 and 7 and the talc 9. As a result of this pressing, the talc 9 is compressed in the direction of the axial line AX, whereby the gas tightness of the interior of the metallic shell 50 is enhanced.

Also, the metallic shell 50 has a shell internal step portion 56 formed on the inner circumference thereof at a position corresponding to the attachment screw portion 52. An insulator step portion 15 of the ceramic insulator 10 located at the base end of the leg portion 13 is pressed against the shell internal step portion 56 with an annular sheet packing 8 interposed therebetween. This sheet packing 8 is a member for maintaining the gas tightness between the metallic shell 50 and the ceramic insulator 10 and prevents leakage of combustion gas.

Figure 3:
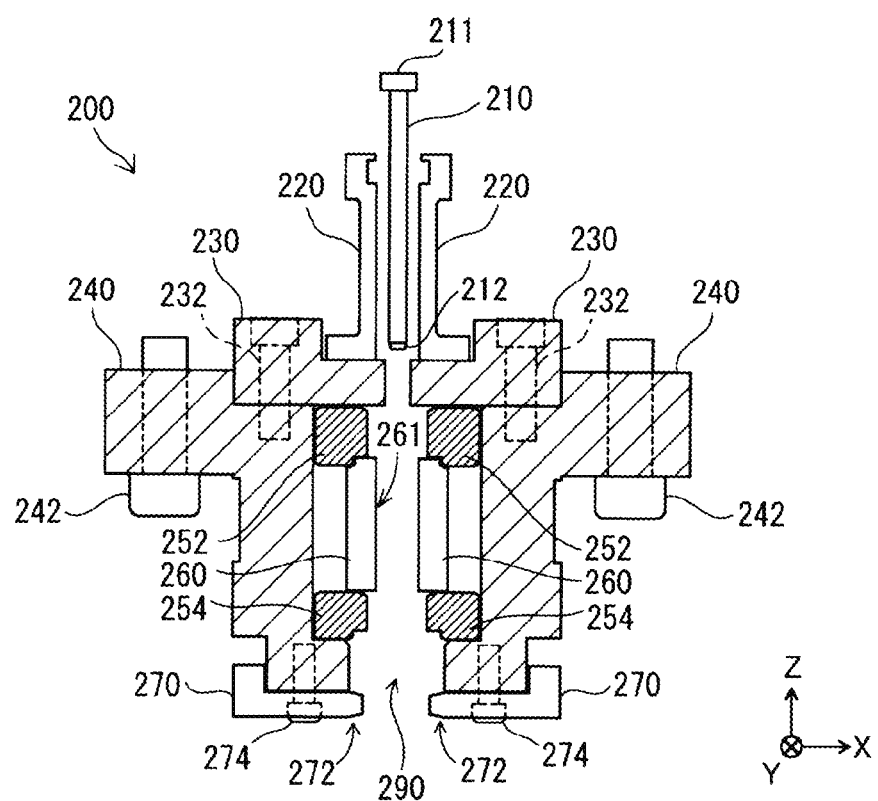
FIG. 3 is an explanatory view showing the specific structure of a pressing and energizing section 200 shown in FIG. 1.

A3. Specific Structure of the Pressing and Energizing Section 200:

FIG. 3 is an explanatory view showing the specific structure of the pressing and energizing section 200 shown in FIG. 1. The pressing and energizing section 200 includes not only the above-described electrically conductive pin 210 but also a guide portion 220, a first support portion 230, first fixing screws 232, a second support portion 240, second fixing screws 242, an upper attachment portion 252, a lower attachment portion 254, and a gripping portion 260. Notably, an electrode member 270 is attached to the foremost end of the pressing and energizing section 200.

The electrically conductive pin 210 has a rod-like external shape and has a flange portion 211 at its end on the base end side. The flange portion 211 has a larger diameter as compared with the remaining portion. The flange portion 211 is in contact with the above-described conductive pin drive section 405 and receives a drive force from the conductive pin drive section 405. The electrically conductive pin 210 has a conductive pin forward end portion 212 at its end on the forward end side. The outer circumferential surface of the conductive pin forward end portion 212 is chamfered. The electrically conductive pin 210 is formed of an electrically conductive material. In the spark plug production process, the electrically conductive w comes into contact with the metallic terminal 40 of the assembly 100 and applies a voltage to the assembly 100. In the present embodiment, the electrically conductive pin 210 is formed of steel (for example, stainless steel, S45C-H, or the like). Notably, instead of steel, other arbitrary electrically conductive materials may be used.

The guide portion 220 has an approximately cylindrical external shape and accommodates the electrically conductive pin 210 in an axial hole at the center. The first support portion 230 has a disk-like external shape, has a through hole formed at the center and extending in the thickness direction (the Z-axis direction), and supports the guide portion 220. The through hole formed at the center of the first support portion 230 communicates with the axial hole of the guide portion 220 in the Z-axis direction. The first support portion 230 is fixed to the second support portion 240 with the first fixing screws 232. The second support portion 240 has an approximately cylindrical external shape and has a flange portion on the base end side. The second support portion 240 is adjacently located on the forward end side of the first support portion 230 and supports the first support portion 230. The second support portion 240 supports the upper attachment portion 252 and the lower attachment portion 254 within an axial hole formed at the center and extending in the Z-axis direction. The second support portion 240 is fixed to the surface of the moving shelf 450 on the vertically lower side thereof with the second fixing screws 242. The electrode member 270 is fixed to the forward end surface of the second support portion 240 with electrode fixing screws 274. The electrode member 270 is formed of an electrically conductive material. In the spark plug production process, the electrode member 270 comes into contact with the metallic shell 50 of the assembly 100 to thereby ground the metallic shell 50. In the present embodiment, the metallic shell 50 is formed of the same steel material as that used to form the electrically conductive pin 210. Notably, the metallic shell 50 may be formed of a steel material which is lower in carbon content than the steel material used to form the electrically conductive pin 210. Also, instead of steel, other arbitrary electrically conductive materials may be used to form the metallic shell 50. The electrode member 270 has a disk-like external shape and has a through hole formed at the center and extending in the thickness direction (the Z-axis direction). In the present embodiment, the edge 272 of the inner circumferential surface of the electrode member 270 forming the through hole is chamfered.

Each of the upper attachment portion 252 and the lower attachment portion 254 has a disk-like external shape and has a through hole formed at the center and extending in the thickness direction (the Z-axis direction). The upper attachment portion 252 and the lower attachment portion 254 are disposed in the axial hole of the second support portion 240. The upper attachment portion 252 is disposed at the end of the axial hole of the second support portion 240 on the base end side such that its outer circumferential surface comes into contact with the inner circumferential surface of the axial hole of the second support portion 240. The lower attachment portion 254 is disposed at the end of the axial hole of the second support portion 240 on the forward end side such that its outer circumferential surface comes into contact with the inner circumferential surface of the axial hole of the second support portion 240. The upper attachment portion 252 and the lower attachment portion 254 support the gripping portion 260 in the Z-axis direction.

In the spark plug production process which will be described later, the gripping portion 260 comes into close contact with the outer circumferential surface of a base end portion of the ceramic insulator 10 and grips the assembly 100. The gripping portion 260 has a cylindrical external shape and has an axial hole 261 formed at the center and extending in the Z-axis direction. The inner diameter of the axial hole 261 is slightly smaller than the outer diameter of the ceramic insulator 10 (the base-end-side trunk portion 18). The gripping portion 260 is fitted between the upper attachment portion 252 and the lower attachment portion 254. Specifically, a radially outer portion of the base end surface of the gripping portion 260 is in contact with a radially inner portion of the forward end surface of the upper attachment portion 252, and a radially outer portion of the forward end surface of the gripping portion 260 is in contact with a radially inner portion of the base end surface of the lower attachment portion 254. The gripping portion 260 corresponds to the insulating member in the claims.

In the present embodiment, of the members which constitute the above-described pressing and energizing section 200, the electrically conductive pin 210 and the second fixing screws 242 are formed of metal, and other members are formed of rubber or resin. Specifically, the second fixing screws 242 are formed of a steel material similar to the steel material used to form the electrically conductive pin 210. The guide portion 220 and the gripping portion 260 are formed of rubber. Examples of the rubber include silicone rubber, acrylic rubber, and butyl rubber. Since the gripping portion 260 is formed of rubber, the gripping portion 260 is deformable so that the gripping portion 260 can freely contract. Each of other members including the first fixing screws 232 are formed of resin. Examples of the resin include Duracon, polyether ether ketone (PEEK), and 66 nylon. Notably, the electrode fixing screws 274 are formed of steel. The reason why the members of the pressing and energizing section 200, excluding the electrically conductive pin 210 and the second fixing screws 242, are formed of rubber or resin is that, in the withstanding voltage test which will be described later, it is necessary to prevent occurrence of flashover between the metallic terminal 40 and the metallic shell 50 through the pressing and energizing section 200.

As shown in FIG. 3, the center axes of the electrically conductive pin 210, the guide portion 220, the first support portion 230, the second support portion 240, the upper attachment portion 252, the lower attachment portion 254, the gripping portion 260, and the electrode member 270 coincide with one another. Therefore, the axial hole of the guide portion 220, the through hole of the first support portion 230, the through hole of the upper attachment portion 252, the axial hole 261 of the gripping portion 260, the through hole of the lower attachment portion 254, and the through hole of the electrode member 270 communicate with one another, whereby the insertion hole 290 is formed.

Figure 4:
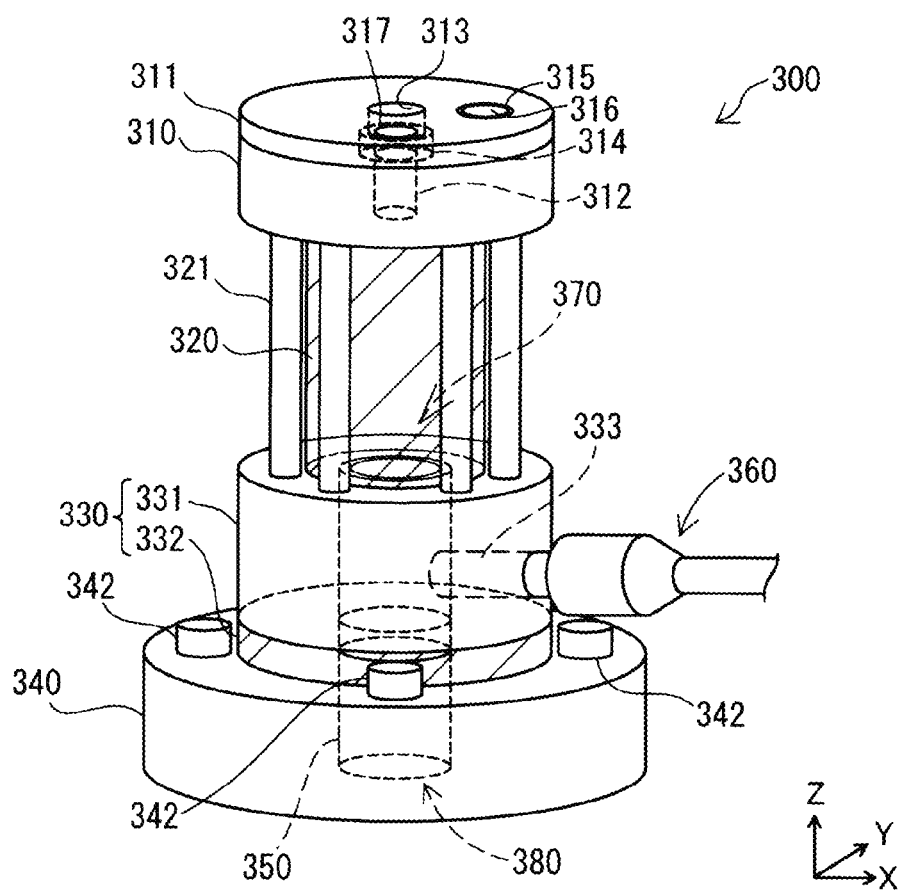
FIG. 4 is a perspective view showing the specific structure of a pressure container 300 shown in FIG. 1.

A4. Specific Structure of the Pressure Container:

FIG. 4 is a perspective view showing the specific structure of the pressure container 300 shown in FIG. 1. The pressure container 300 includes an upper support portion 310, a seal 314, a seal holder 311, a forward end accommodation portion 320, a plurality of supporting columns 321, a center support portion 330, and a lower support portion 340.

The upper support portion 310 is located on the vertically upper side (the base end side) of the pressure container 300 and has an approximately circular columnar external shape. An accommodation hole 312 is formed at the center of the upper support portion 310. The accommodation hole 312 is a through hole which penetrates the upper support portion 310 in the thickness direction (the Z-axis direction). In the withstanding voltage test which will be described later, a portion of the assembly 100 on the forward end side; more specifically, a portion of the assembly 100 corresponding to a portion of the attachment screw portion 52 on the base end side, is accommodated in the accommodation hole 312. The diameter of the accommodation hole 312 is greater than the diameter of the screw thread of the attachment screw portion 52. In the upper support portion 310, a hole having a larger diameter as compared with the accommodation hole 312 is provided at the base end of the accommodation hole 312, and a seal 314 is accommodated therein. The seal 314 has a ring-like external shape and has an axial hole formed therein. The seal 314 is accommodated in the larger-diameter hole of the upper support portion 310 such that the center axis of the seal 314 coincides with the axis of the accommodation hole 312. The axial hole of the seal 314 has a diameter approximately equal to that of the accommodation hole 312 and communicates with the accommodation hole 312 in the vertical direction. Like the accommodation hole 312, the axial hole of the seal 314 accommodates the portion of the assembly 100 on the forward end side in the withstanding voltage test. In the following description, the axial hole of the seal 314 and the accommodation hole 312 may be collectively referred to as the accommodation hole 312. In the withstanding voltage test, the seal 314 comes into contact with the assembly 100 (the forward end surface 55 of the seal portion 54) to thereby seal the opening of the chamber 370. The above-described "opening of the chamber 370" is an opening sealed by the assembly 100, and in the present embodiment, means the upper end opening 317 of the axial hole of the seal 314. The seal 314 may be formed of, for example, resin or rubber, such as urethane, or Teflon (registered trademark).

The seal holder 311 has an approximately circular columnar external shape and is smaller in thickness than the upper support portion 310. The outer diameter of the seal holder 311 is approximately equal to that of the upper support portion 310. The seal holder 311 is disposed on and in contact with the upper end surface of the upper support portion 310 such that its center axis coincides with the center axis of the upper support portion 310, and is fixed to the upper support portion 310 with a fixing screw 316. Notably, the head of the fixing screw 316 is accommodated in a screw accommodation hole 315 formed on the upper end surface of the seal holder 311. A through hole 313 is formed at the center of the seal holder 311 and extends in the thickness direction. The diameter of the through hole 313 is greater than the diameters of the accommodation hole 312 and the axial hole of the seal 314 and is smaller than the outer diameter of the seal 314. The through hole 313 communicates with the accommodation hole 312 in the vertical direction. In the withstanding voltage test, a portion of the assembly 100; specifically, a portion of the seal portion 54, is accommodated in the through hole 313. The seal holder 311 is fixed to the upper support portion 310. Thus, the seal holder 311 presses the seal 314 from the vertically upper side to thereby restrict its movement in the vertical direction (the Z-axis direction).

The forward end accommodation portion 320 has a cylindrical external shape and is disposed on the vertically lower side of the upper support portion 310 such that the forward end accommodation portion 320 is located adjacent to the upper support portion 310. The forward end accommodation portion 320 is formed of a transparent resin material. The axial line of the forward end accommodation portion 320 coincides with the axial line of the upper support portion 310. The space inside the forward end accommodation portion 320 communicates with the accommodation hole 312. In the withstanding voltage test which will be described later, the forward end accommodation portion 320 accommodates a forward end portion of the assembly 100; more specifically, a portion corresponding to a portion of the attachment screw portion 52 on the forward end side and a portion (the center electrode 20, a portion of the leg portion 13, and the ground electrode 30) located on the forward end side of that portion. The outer diameter of the forward end accommodation portion 320 is smaller than the outer diameter of the upper support portion 310. The plurality of supporting columns 321 are disposed at predetermined intervals in the circumferential direction so as to surround the forward end accommodation portion 320. Each supporting column 321 is a thin circular columnar member, and is connected at its one end to the lower end surface of the upper support portion 310 and connected at its other end to the upper end surface of the center support portion 330.

The center support portion 330 has an approximately circular columnar external shape and is disposed on the vertically lower side of the forward end accommodation portion 320 such that the center support portion 330 is located adjacent to the forward end accommodation portion 320. The outer diameter of the center support portion 330 is approximately equal to the outer diameter of the upper support portion 310. The center support portion 330 includes a main support portion 331 and a viewing portion 332. The main support portion 331 is disposed in contact with the forward end accommodation portion 320 and is connected to a pipe 360. The main support portion 331 has a communication hole 333 for establishing communication between a connection portion of the pipe 360 and a center hole 350 which will be described later. The viewing portion 332 is disposed in contact with the lower end surface of the main support portion 331. The upper end surface of the viewing portion 332 and the lower end surface of the main support portion 331 are joined together. Also, the lower end surface of the viewing portion 332 is joined to the upper end surface of the lower support portion 340. The entirety of the viewing portion 332 is substantially transparent and is configured such that the interior of the viewing portion 332 can be viewed. The viewing portion 332 may be formed of, for example, a material similar to the material used to form the window provided in the bottom portion 380 of the chamber 370.

The lower support portion 340 has an approximately circular columnar external shape and is disposed on the vertically lower side of the center support portion 330 such that the lower support portion 340 is located adjacent to the center support portion 330. The outer diameter of the lower support portion 340 is greater than the outer diameter of the center support portion 330. The lower support portion 340 is fixed to the lower fixed plate 410 with a plurality of fixing screws 342. The center hole 350 is formed to extend through the center support portion 330 and the lower support portion 340. The upper end of the center hole 350 communicates with the internal space of the forward end accommodation portion 320. An end portion of the center hole 350 on the vertically lower side corresponds to the above-described bottom portion 380 and faces the through hole 412 of the lower fixed plate 410.

The accommodation hole 312 and the internal space of the forward end accommodation portion 320 communicate with each other in the vertical direction, and the above-described chamber 370 is formed inside the pressure container 300. An unillustrated air compressor is connected to the pipe 360, and compressed air is supplied to the chamber 370 through the pipe 360, whereby the pressure within the chamber 370 is increased. In the withstanding voltage test which will be described later, only a portion of the assembly 100 on the forward end side is accommodated in the chamber 370. Therefore, the size of the pressure container 300 is smaller as compared with a container having a chamber which accommodates the entirety of the assembly 100.

Figure 5:
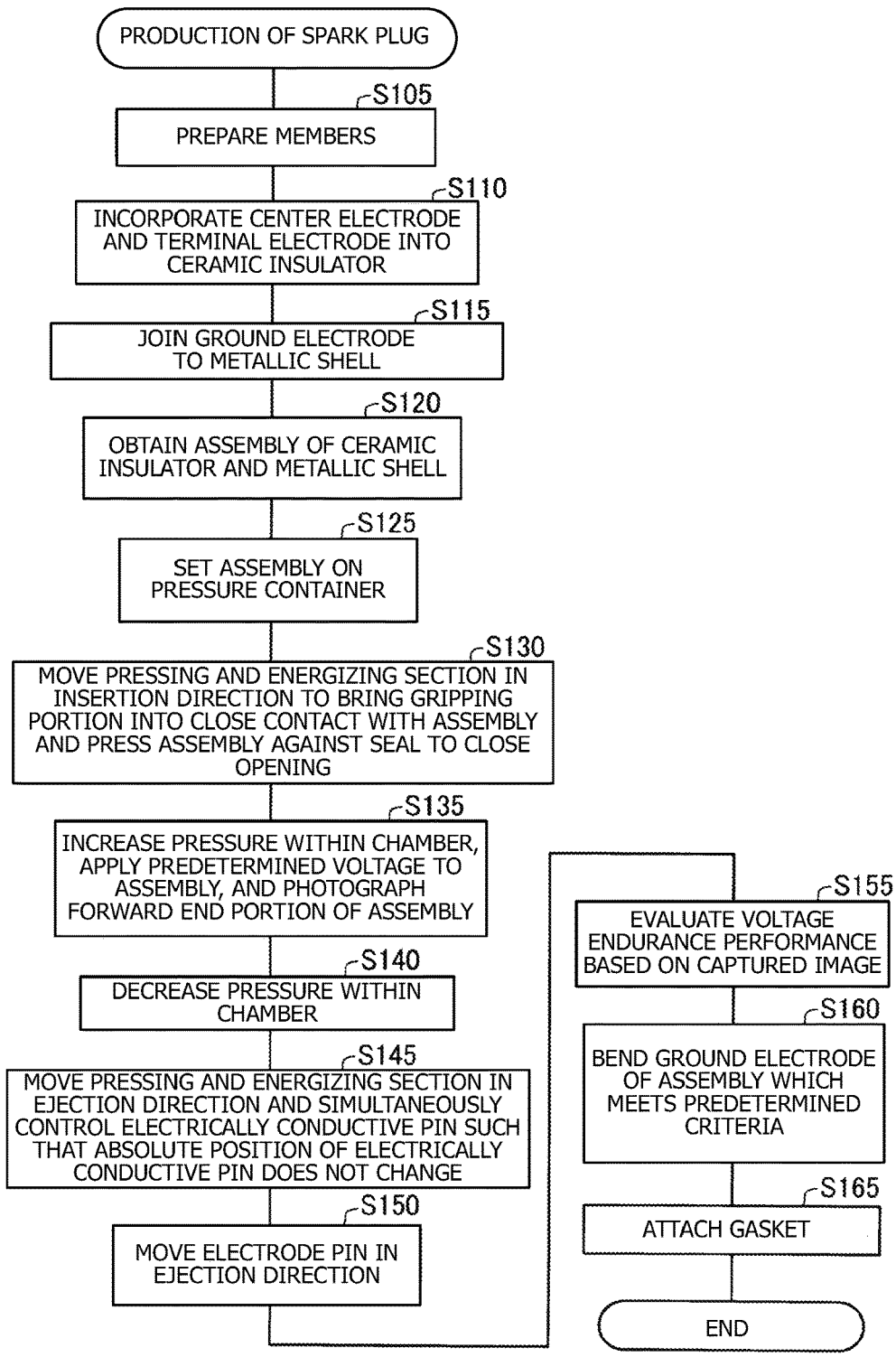
FIG. 5 is a flowchart showing the steps of a spark plug production method which is one embodiment of the present invention.

A5. Spark Plug Production Method:

FIG. 5 is a flowchart showing the steps of a spark plug production method which is one embodiment of the present invention. When a spark plug is produced, members which constitutes the spark plug are first prepared (step S105). The center electrode 20 and the metallic terminal 40 are inserted into the axial hole 12 of the ceramic insulator 10, whereby the center electrode 20 and the metallic terminal 40 are combined with the ceramic insulator 10 (step S110). Notably, within the axial hole 12, the seals 4a and 4b and the ceramic resistor 3 are disposed between center electrode 20 and the metallic terminal 40. The ground electrode 30 is joined to the forward end surface 57 of the metallic shell 50 (step S115). After step S115, the metallic shell 50 and the ground electrode 30 may be plated. The ceramic insulator 10 having the center electrode 20 and the metallic terminal 40 incorporated therein in step S110 is combined with the metallic shell 50 to obtain the assembly 100 shown in FIG. 2 (step S120).

A forward end portion of the assembly 100 is inserted into the pressure container 300 from the upper end of the through hole 313 of the seal holder 311 so as to set the assembly 100 onto the pressure container 300 (step S125). As described above, the inner diameter of the accommodation hole 312 is greater than the outer diameter of the screw thread of the metallic shell 50 of the assembly 100. Therefore, the assembly 100 can be easily set onto the pressure container 300 by inserting the forward end portion of the assembly 100 into the through hole 313 and the accommodation hole 312 from the upper end of the through hole 313. Accordingly, the assembly 100 can be set within a shorter time and wearing of the attachment screw portion 52 can be suppressed as compared with, for example, a configuration in which the assembly 100 is set onto the pressure container 300 by screwing the attachment screw portion 52 into the accommodation hole 312. Notably, FIG. 1 shows the states of the spark plug production device 500 and the assembly 100 immediately after step S125 has been executed. Namely, the assembly 100 is set onto the pressure container 300 and the pressing and energizing section 200 is disposed on the vertically upper side of the assembly 100. As a result of execution of step S125, the opening of the chamber 370; namely, the opening 317 of the seal 314, is closed by the seal portion 54 (the forward end surface 55) of the assembly 100. However, at this point in time, the gas tightness of the interior of the chamber 370 has not yet been secured.

In the state shown in FIG. 1; in other words, in a state before the gripping portion 260 of the pressing and energizing section 200 comes into close contact with the outer circumferential surface of a base end portion of the assembly 100 (the ceramic insulator 10), the axial line of the assembly 100, the axial line of the opening 317 (an imaginary line which passes through the center of the opening 317 and is parallel to a perpendicular of a plane containing the opening 317), the axial line of the gripping portion 260, and the axial line of the electrically conductive pin 210 coincide with one another. Notably, the state in which the axial lines coincide with one another does not mean only a state in which the axial lines completely coincide with one another and it is sufficient that these axial lines approximately coincide with one another. Accordingly, when the pressing and energizing section 200 is moved downward in the insertion direction in step S130 which will be described later, the axial line of the assembly 100 and the axial line of the gripping portion 260 can be easily rendered coincident with each other. If the gripping portion 260 is attached to the assembly 100 in a state in which the axial line of the assembly 100 (the ceramic insulator 10) and the axial line of the gripping portion 260 are inclined with respect to each other, the degree of close contact between the gripping portion 260 and the assembly 100 decreases, whereby flashover along the outer circumferential surface of the ceramic insulator 10 becomes more likely to occur. In contrast, in the present embodiment, since the axial line of the assembly 100 and the axial line of the gripping portion 260 can be easily rendered coincident with each other as described above, occurrence of the above-mentioned flashover can be prevented. Also, when the pressing and energizing section 200 is moved downward in the insertion direction in step S130 which will be described later, the axial line of the assembly 100 and the axial line of the opening 317 can be easily rendered coincident with each other. If the seal 314 is pressed by the assembly 100 in a state in which the axial line of the assembly 100 and the axial line of the opening 317 are inclined with respect to each other, pressure escapes, and the degree of gas tightness of the pressure container 300 decreases. In contrast, in the present embodiment, since the axial line of the assembly 100 and the axial line of the opening 317 can be easily rendered coincident with each other as described above, a decrease in the degree of gas tightness of the pressure container 300 can be suppressed. Therefore, the pressure within the pressure container 300 can be made very high in step S135 which will be described later, and application of higher voltage to the assembly 100 can be realized.

By moving the pressing and energizing section 200 (downward) in the insertion direction, the gripping portion 260 is brought into close contact with the assembly 100 and the assembly 100 (the forward end surface 55 of the metallic shell 50) is pressed against the upper end surface of the seal 314, whereby the opening 317 is sealed by the assembly 100 (step S130).

Figure 6:
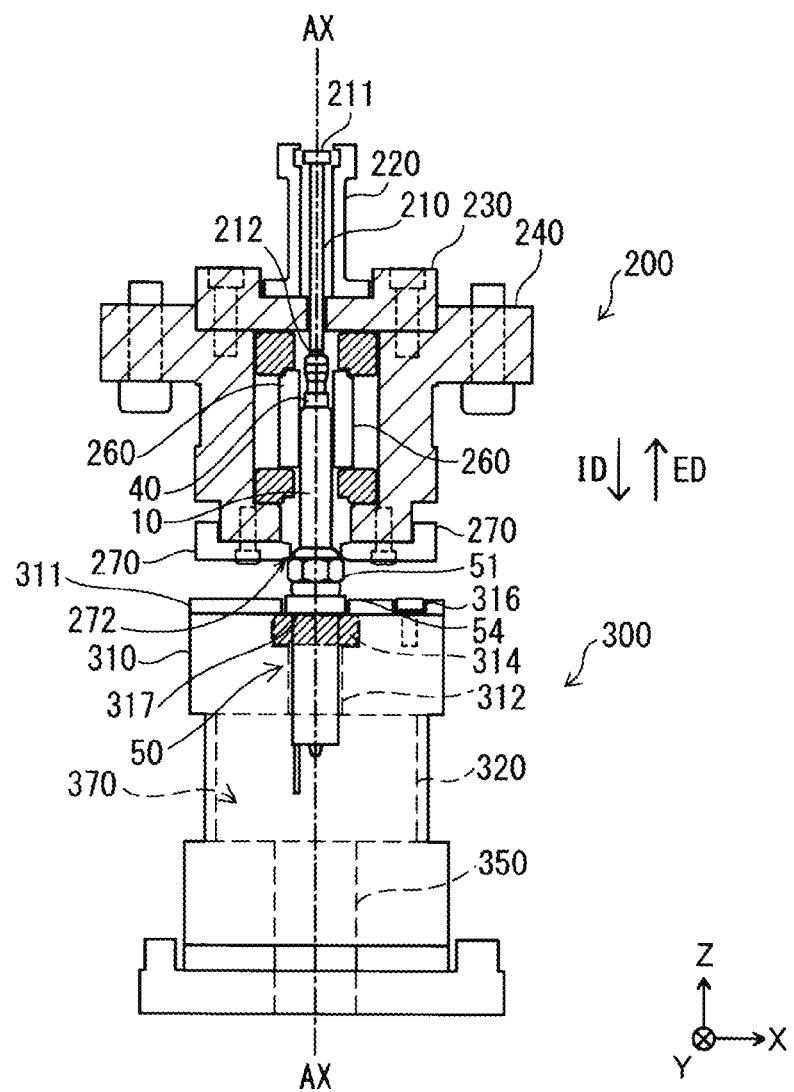
FIG. 6 is an explanatory view showing the states of the spark plug production device 500 and the assembly 100 during execution of step S130.

FIG. 6 is an explanatory view showing the states of the spark plug production device 500 and the assembly 100 during execution of step S130. In FIG. 6, of the spark plug production device 500, only the pressing and energizing section 200 and the pressure container 300 are shown for convenience of description. As shown in FIG. 6, step S130 is executed in a state in which the axial line of the opening 317 and the axial line AX of the assembly 100 coincide with each other.

When the pressing and energizing section 200 moves in the insertion direction ID from the state shown in FIG. 1, a base end portion of the assembly 100 is inserted into the insertion hole 290 of the pressing and energizing section 200. When such movement proceeds, the ceramic insulator 10 is inserted into the axial hole 261 of the gripping portion 260. The inner diameter of the axial hole 261 is smaller than the outer diameter of the ceramic insulator 10. However, since the gripping portion 260 is formed of rubber, the axial hole 261 is expanded in the radial direction, and the ceramic insulator 10 is inserted. As a result, as shown in FIG. 6, the gripping portion 260 comes into close contact with a base end portion of the ceramic insulator 10 over the entire circumference thereof. Notably, in the present embodiment, the gripping portion 260 does not come into close contact with the metallic terminal 40. However, the shape of the inner circumference of the gripping portion 260 may be changed such that the gripping portion 260 comes into close contact with the metallic terminal 40. In order to prevent flashover more reliably, it is preferred that the gripping portion 260 be brought into close contact with both the ceramic insulator 10 and the metallic terminal 40.

In the state in which the gripping portion 260 is in close contact with the base end portion of the ceramic insulator 10, the edge 272 of the electrode member 270 comes into contact with the upper end surface of the tool engagement portion 51. In step S130, even after the electrode member 270 has come into contact with the tool engagement portion 51, the pressing and energizing section 200 continuously presses the assembly 100 in the insertion direction ID through the electrode member 270. The pressing force at that time is a force set such that the interior of the chamber 370 can endure a pressure increase to 5 MPa, and is, for example, a force of 300 kgw. When the pressing and energizing section 200 is moved in the insertion direction ID so as to seal the opening 317 of the chamber 370 by the assembly 100, the axial line AX of the assembly 100 and the axial line of the opening 317 coincide with each other. Accordingly, in the present embodiment, the direction in which the assembly 100 is pressed (the insertion direction ID) is opposite the direction in which air leaks from the opening 317 of the chamber 370; i.e., the +Z direction (an ejection direction ED). Therefore, the degree of sealing of the opening 317 by the assembly 100 can be increased, and the gas tightness can be secured, for example, even when the internal pressure of the chamber 370 is increased to about 10 MPa (mega pascal) required in the engine head. Also, a pressure application axis, along which pressure is applied to the assembly 100 so as to press the assembly 100, and the center axis (close contact axis) of the opening 317 to be sealed coincide with each other. Specifically, the center axes (pressure application axis) of the electrically conductive pin 210, the guide portion 220, the first support portion 230, the second support portion 240, the upper attachment portion 252, the lower attachment portion 254, the gripping portion 260, and the electrode member 270 coincide with the center axis (close contact axis) of the opening 317. Therefore, as compared with a configuration in which the pressure application axis and the close contact axis deviate from each other, the rigidity of the pressing and energizing section 200 required to secure the same degree of gas tightness can be made lower. Therefore, many constituent elements of the pressing and energizing section 200 can be formed of rubber or resin, and thus, the pressing and energizing section 200 can be reduced in size and weight.

As a result of step S130, the assembly 100 comes into close contact with the pressure container 300 along the axial line AX of the assembly 100. Notably, in the present embodiment, since the axial line of the chamber 370 coincides with the axial line of the opening 317, step S130 is executed in a state in which the axial line AX of the assembly 100 and the axial line of the chamber 370 coincide with each other. During execution of a step (step S135) subsequent to step S130, the pressing of the assembly 100 in the insertion direction ID by the pressing and energizing section 200 is continued.

As shown in FIG. 6, in the present embodiment, when step S130 is executed, the electrically conductive pin 210 also moves in the insertion direction ID, and the forward end of the electrically conductive pin 210 comes into contact with the metallic terminal 40 and presses the metallic terminal 40 in the insertion direction ID. Notably, the pressing force at that time is smaller than the pressing force with which the pressing and energizing section 200 presses the metallic shell 50 (the tool engagement portion 51) in the insertion direction ID through the electrode member 270.

Air is supplied from the unillustrated air compressor into the chamber 370 to thereby increase the pressure within the chamber 370, a predetermined voltage is applied to the assembly 100, and a forward end portion of the assembly 100 is photographed by the unillustrated image-capturing device (step S135). Since only the portion of the assembly 100 located on the forward end side of the seal portion 54 is accommodated in the chamber 370, the volume of the chamber 370 is smaller than that of a container configured to accommodate the entirety of the assembly 100. Therefore, the operation of increasing the pressure within the chamber 370 is completed within a short period of time. Specifically, the voltage application and photographing in step S135 may be performed as follows. Namely, a relatively high voltage of 30 to 40 kV (kilovolt) is applied between the metallic terminal 40 (and the center electrode 20 electrically connected to the metallic terminal 40) and the metallic shell 50 through the electrically conductive pin 210 and the electrode member 270, and the forward end portion of the assembly 100 is photographed every time the voltage is applied. The voltage application and photographing are repeated a plurality of times (for example, several hundreds of times). In the case where the ceramic insulator 10 does not have a defect such as a pinhole, since the center electrode 20 and the ground electrode 30 are separated from each other by a distance greater than the spark discharge gap, spark discharge does not occur. In contrast, in the case where the ceramic insulator 10 has a defect, since spark discharge occurs through such a defect, spark discharge appears on the captured image of the forward end portion of the assembly 100. At that time, since the gripping portion 260, which is an insulating member, is in close contact with the base end portion of the ceramic insulator 10, it is possible to prevent occurrence of so-called flashover which is a phenomenon in which discharge occurs between the metallic terminal 40 and the metallic shell 50 such that the discharge creeps along the surface of the base end portion of the ceramic insulator 10. Notably, even in the case where flashover occurs, no spark discharge occurs on the forward end side of the assembly 100 and the image captured through photographing contains no spark. In this case, the voltage of the assembly 100 is measured, and the determination as to whether or not flashover occurs can be made on the basis of the waveform of the measured voltage. After completion of the above-described step S135, the pressure within the chamber 370 is decreased (step S140).

The pressing and energizing section 200 is then moved in the ejection direction ED by a predetermined distance, and during this movement, the electrically conductive pin 210 is controlled such that the absolute position of the electrically conductive pin 210 does not change (step S145). In other words, the conductive pin drive section 405 moves the electrically conductive pin 210 relative to the pressing and energizing section 200 such that the absolute position of the electrically conductive pin 210 does not change.

Figure 7:
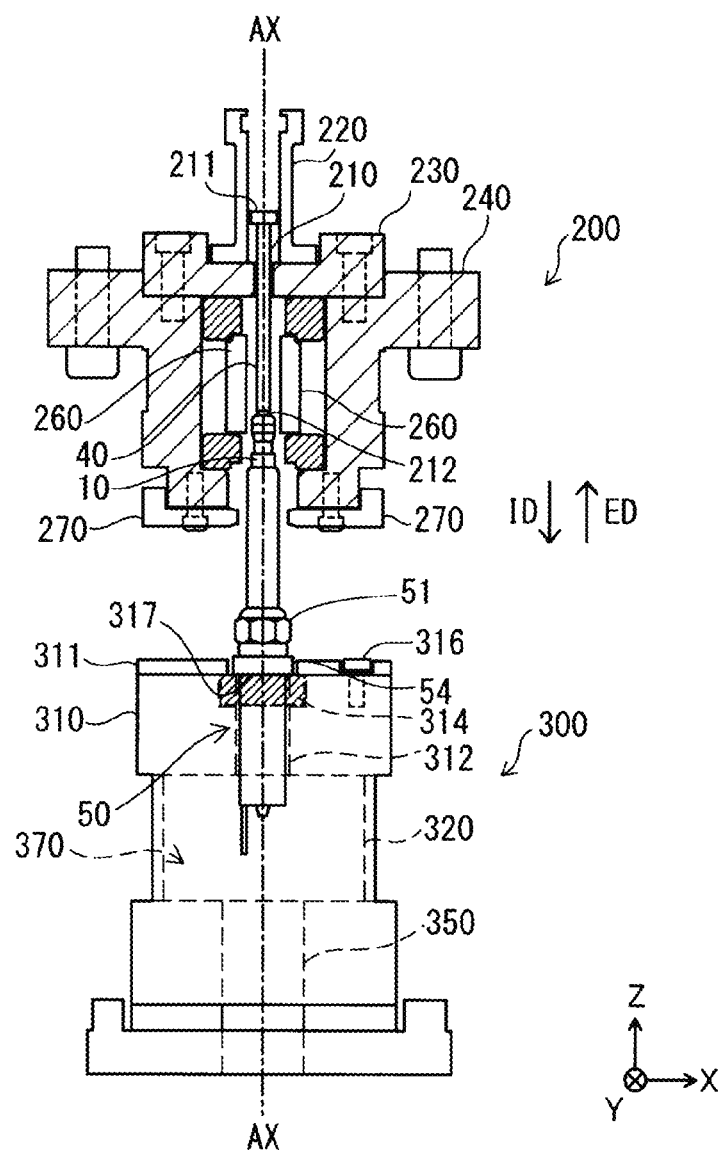
FIG. 7 is an explanatory view showing the states of the spark plug production device 500 and the assembly 100 during execution of step S145.

FIG. 7 is an explanatory view showing the states of the spark plug production device 500 and the assembly 100 during execution of step S145. As shown in FIG. 7, when step S145 is executed, the pressing and energizing section 200 moves in the ejection direction ED (upward in the vertical direction) while maintaining the state in which the electrically conductive pin 210 presses the metallic terminal 40 in the insertion direction ID (downward). As a result of such an operation, with the position of the assembly 100 (the ceramic insulator 10) remaining the same, the gripping portion 260 moves, together with the pressing and energizing section 200, toward the base end side in relation to the ceramic insulator 10. Therefore, the gripping portion 260 is disengaged from the ceramic insulator 10. Notably, the moving distance of the electrically conductive pin 210 within the voltage application section 400 and the pressing and energizing section 200 is set such that the positional relation between the electrically conductive pin 210 and the assembly 100 (the metallic terminal 40) does not change due to movement of the pressing and energizing section 200.

After completion of step S145, the electrically conductive pin 210 is moved upward in the ejection direction ED and is returned to the state shown in FIG. 1 (step S150). The above-described steps S125 through S150 correspond to the withstanding voltage test for the assembly 100; namely, the method of inspecting the assembly 100.

On the basis of the captured image obtained in step S135, the voltage endurance performance of the assembly 100 is evaluated (step S155). For example, among the large number of captured images obtained in step S135, images including no spark discharge are counted. When the number of the images including no spark discharge is equal to or greater than a threshold value, the assembly 100 is evaluated to be high in voltage endurance performance. When the number of the images including no spark discharge is less than the threshold value, the assembly 100 is evaluated to be low in voltage endurance performance. The threshold value may be determined, for example, by evaluating an assembly 100 into which a ceramic insulator 10 having a defect has been incorporated in advance. When the result of the evaluation in step S155 shows that the assembly 100 satisfies predetermined criteria, the ground electrode 30 of the assembly 100 is bent. Specifically, the ground electrode 30 is bent such that the distal end of the ground electrode 30 approaches the center electrode 20. In the present embodiment, the ground electrode 30 is bent such that the forward end surface of the center electrode 20 faces an inner side surface of a distal end portion of the ground electrode 30. At that time, the bending work is performed such that the gap between the forward end surface of the center electrode 20 and the ground electrode 30; i.e., the spark discharge gap, has a predetermined dimension. Notably, instead of bending the ground electrode 30 in the above-described manner, the ground electrode 30 may be bent such that the distal end surface of the ground electrode 30 faces the outer circumferential surface of a forward end portion of the center electrode 20.

An unillustrated gasket is attached such that the gasket comes into contact with the forward end surface 55 of the seal portion 54 (step S165). For example, an annular gasket formed by folding a metal plate may be used as the above-mentioned gasket. The gasket can be attached to the metallic shell 50 by inserting the attachment screw portion 52 of the metallic shell 50 into the center hole of the gasket. Since the gasket is attached after the withstanding voltage test, it is possible to prevent lowering of the sealing performance of the gasket which would otherwise occur when the assembly 100 comes into close contact with the pressure container 300 in the withstanding voltage test. The lowering of the sealing performance of the gasket occurs due to damage to the gasket or a decrease in the resilience force of the gasket along the axial line AX when the assembly 100 comes into close contact with the pressure container 300. When step S165 ends, a spark plug is completed.

In the above-described spark plug production method of the first embodiment, since only a portion of the assembly 100 on the forward end side is accommodated in the chamber 370, attachment of the assembly 100 to the pressure container 300 and removal of the assembly 100 from the pressure container 300 can be performed within a short period of time. Also, since the volume of the chamber 370 can be decreased, the pressurization and depressurization of the interior of the chamber 370 can be performed within a short period of time. As a result of these, the time required for production of the spark plug can be shortened. Also, since only a single assembly 100 is attached to the pressure container 300, the volume of the chamber 370 can be made smaller as compared with a container (the pressure container 300) to which a plurality of assemblies 100 are attached. Notably, in the case where a large number of assemblies 100 are processed simultaneously in the present embodiment, chambers 370 (pressure containers 300) the number of which is equal to the number of assemblies 100 processed simultaneously are prepared, whereby the production time per spark plug can be shortened as in the case of the above-described embodiment.

Also, since the volume of the chamber 370 can be decreased, the size of the pressure container 300 can be decreased. In addition, since the surface area of the chamber 370 can be decreased, it is unnecessary to use a material having an extremely high rigidity in order to increase the rigidity of the entire pressure container 300 or use a complex and large mechanism or member so that the pressure container 300 has a robust structure. Therefore, increases in the size and production cost of the pressure container 300 can be suppressed.

Also, since the opening 317 of the chamber 370 is sealed through use of the assembly 100, the number of steps can be decreased as compared with the case where setting of the assembly 100 onto the pressure container 300 and sealing of the opening 317 of the chamber 370 are performed in different steps, whereby the time required for producing the spark plug can be shortened. In addition, since the electrically conductive pin 210 is movably disposed in the insertion hole 290 of the pressing and energizing section 200, it is possible to move the pressing and energizing section 200 in the insertion direction ID, to thereby press the assembly 100 by the pressing and energizing section 200, and simultaneously bring the electrically conductive pin 210 into contact with the metallic terminal 40 of the assembly 100. Therefore, the number of steps can be decreased as compared with the case where the operation of pressing the assembly 100 by the pressing and energizing section 200 and the operation of bringing the electrically conductive pin 210 into contact with the metallic terminal 40 are performed in different steps, whereby the time required to produce the spark plug can be shortened. Similarly, since the electrode member 270 is disposed at the forward end portion of the pressing and energizing section 200, it is possible to move the pressing and energizing section 200 in the insertion direction ID, to thereby press the assembly 100 by the pressing and energizing section 200, and simultaneously bring the electrode member 270 into contact with the metallic shell 50. Therefore, the number of steps can be decreased as compared with the case where the operation of pressing the assembly 100 by the pressing and energizing section 200 and the operation of bringing the electrode member 270 into contact with the metallic shell 50 are performed in different steps, whereby the time required to produce each spark plug can be shortened.

Also, since the opening 317 of the chamber 370 is sealed by pressing the pressure container 300 (the seal 314) by the assembly 100, it is unnecessary to attain gas tightness by bringing the assembly 100 into screw engagement with the pressure container 300 (the accommodation hole 312) through utilization of the attachment screw portion 52 of the metallic shell 50. Therefore, the time required to set the assembly 100 onto the pressure container 300 can be shortened, and damage to or wearing of the attachment screw portion 52 can be prevented.

Also, since the pressing of the assembly 100 by the pressing and energizing section 200 and the attachment of the gripping portion 260 to the ceramic insulator 10 are performed in a state in which the axial line of the opening 317 of the chamber 370 and the axial line AX of the assembly 100 coincide with each other, it is possible to prevent the assembly 100 from closing the opening 317 in a misaligned condition and to prevent the gripping portion 260 from being attached to the ceramic insulator 10 in a misaligned condition. Since the assembly 100 is prevented from closing the opening 317 in a misaligned condition, the gas tightness of the pressure container 300 can be improved when the assembly 100 is pressed against the seal 314. Therefore, the interior of the pressure container 300 can be pressurized to a very high pressure, and application of higher voltage to the assembly 100 can be realized. Also, since the gripping portion 260 is prevented from being attached to the ceramic insulator 10 in a misaligned condition, occurrence of flashover along the outer circumferential surface of the ceramic insulator 10 can be prevented.

Also, the pressing and energizing section 200 moves only in the Z-axis direction; namely, upward or downward in the vertical direction, and does not move in the horizontal direction. Therefore, the processing time can be shortened as compared with a configuration in which the pressing and energizing section 200 moves in the horizontal direction. Also, since the direction in which the assembly 100 is pressed (the insertion direction ID) is opposite the direction in which air is apt to leak from the opening 317 of the chamber 370, the degree of sealing of the opening 317 by the assembly 100 can be improved. Also, the pressure application axis, along which pressure is applied to the assembly 100 so as to press the assembly 100, coincides with the center axis (the close contact axis) of the opening 317 to be sealed. Therefore, as compared with a configuration in which the pressure application axis and the close contact axis deviate from each other, the rigidity of the pressing and energizing section 200 required to secure the same degree of gas tightness can be made lower. Therefore, many constituent elements (all the members excluding the electrically conductive pin 210 and the second fixing screws 24) of the pressing and energizing section 200 can be formed of rubber or resin. As a result, occurrence of flashover can be prevented, whereby application of higher voltage to the assembly 100 can be realized, and, in addition, reduction in the size and weight of the pressing and energizing section 200 can be realized.

Also, the gripping portion 260 whose inner diameter is smaller than the outer diameter of the ceramic insulator 10 is formed of rubber, and the ceramic insulator 10 is inserted into the axial hole 261 of the gripping portion 260 by pressing the gripping portion 260 against the ceramic insulator 10 along the axial line AX of the assembly 100. Therefore, the gripping portion 260 can be brought into close contact with the ceramic insulator 10 along the axial line AX of the assembly 100, whereby improved close contact can be established between the gripping portion 260 and the ceramic insulator 10. Accordingly, as compared with a configuration in which an insulating member is merely pressed against the ceramic insulator 10 in the radial direction, the gripping portion 260 can be brought into close contact with the ceramic insulator 10 uniformly in the circumferential direction, whereby improved close contact can be established. Therefore, flashover can be prevented more reliably.

Also, in step S145, the pressing and energizing section 200 moves in the ejection direction ED (upward in the vertical direction) while maintaining the state in which the electrically conductive pin 210 presses the metallic terminal 40 in the insertion direction ID (downward). Therefore, the assembly 100 is prevented from moving upward together with the pressing and energizing section 200, and the gripping portion 260 can be disengaged from the ceramic insulator 10. In addition, unlike a configuration in which such relative movement between the gripping portion 260 and the ceramic insulator 10 is realized by moving the assembly 100 downward together with the pressure container 300 without changing the position of the gripping portion 260, a configuration for engaging the assembly 100 and the pressure container 300 with each other becomes unnecessary, whereby the structure of the spark plug production device 500 can be simplified.

Also, since a viewing window is provided in the bottom portion 380 of the pressure container 300 and the bottom portion 380 faces the through hole 412 formed in the lower fixed plate 410, the forward end of the assembly 100 can be photographed at the through hole 412. Therefore, the determination as to whether or not the ceramic insulator 10 has a defect can be easily made through use of the obtained image.

Also, since the withstanding voltage test can be performed before the ground electrode 30 is bent, the distance between the ground electrode 30 and the center electrode 20 at the time of execution of the withstanding voltage test can be made relatively large. Therefore, a very high voltage can be applied in the withstanding voltage test.

Also, the peripheral edge of the forward end of the electrically conductive pin 210 and the edge 272 of the inner circumferential surface of the electrode member 270 are chamfered. These edges are portions which come into contact with the metallic terminal 40 or the metallic shell 50 and may become a starting point (or an ending point) of flashover. However, since these edges are chamfered, occurrence of flashover which starts from or ends at these edges can be prevented.

Also, in step S130, the assembly 100 comes into close contact with the chamber 370 in the direction of the axial line of the assembly 100 (in the insertion direction) through the seal 314. Thus, the gas tightness of the chamber 370 can be improved. Therefore, the pressure within the pressure container 300 (within the chamber 370) can be increased, and application of higher voltage between the metallic terminal 40 and the metallic shell 50 can be realized. Also, it is possible to prevent the assembly 100 (the metallic shell 50) from being damaged by the pressure container 300 when the assembly 100 is pressed against the pressure container 300.

B. Modifications

B1. Modification 1:

In the above-described embodiment, the portion of the assembly 100 located on the forward end side of the seal portion 54 is accommodated in the chamber 370. However, the present invention is not limited thereto. It is sufficient that at least the gap 31 formed between the inner circumferential surface of the axial hole of the metallic shell 50 and the outer circumferential surface of the leg portion 13 of the ceramic insulator 10 is accommodated in the chamber 370.

B2. Modification 2:

In step S135 of the above-described embodiment, a forward end portion of the assembly 100 applied with high voltage is photographed. However, instead of photographing, a tester may visually observe the forward end portion of the assembly 100 through the through hole 412 or the forward end accommodation portion 320. In this case as well, the determination as to whether or not spark discharge occurs at the forward end portion can be made. Also, photographing is performed through the window provided in the bottom portion 380 of the chamber 370. However, photographing may be performed through the viewing portion 332.

B3. Modification 3:

In step S145 of the above-described embodiment, in order to disengage the gripping portion 260 from the ceramic insulator 10, the pressing and energizing section 200 is moved in the ejection direction ED by a predetermined distance, and simultaneously, the electrically conductive pin 210 is moved relative to the pressing and energizing section 200. However, the present invention is not limited thereto.

The gripping portion 260 may be disengaged from the ceramic insulator 10 by moving the assembly 100 and the pressure container 300 downward through employment of a configuration in which the pressure container 300 and the lower fixed plate 410 can move in the Z-axis direction and the assembly 100 and the pressure container 300 can engage with each other. Namely, in general, at least one of the gripping portion 260 and the ceramic insulator 10 may be displaced such that the gripping portion 260 relatively moves, along the axial line AX of the assembly 100, in relation to the ceramic insulator 10 from the forward end toward the base end of the assembly 100.

B4. Modification 4:

In the above-described embodiment, both the step of bending the ground electrode 30 (step S160) and the step of attaching a gasket (step S165) are performed after the withstanding voltage test (steps S125 through S150). However, these steps may be performed before the withstanding voltage test.

B5. Modification 5:

In the above-described embodiment, the voltage applied in step S135 is a voltage which does not cause generation of spark discharge on the forward end side of the assembly 100. However, the applied voltage may be a high voltage which causes generation of spark discharge. In this case, in a normal state, flashover occurs along the surface of the leg portion 13 so that spark is generated at the forward end surface of the ceramic insulator 10 (the leg portion 13). Accordingly, in the case where the image captured through photographing includes spark generated at such a portion, the assembly 100 can be determined to be normal. In contrast, in the case where the ceramic insulator 10 has a through hole stemming from a defect such as a pinhole, discharge occurs through the through hole. Therefore, no spark is generated at the forward end surface of the ceramic insulator 10 (the leg portion 13). Accordingly, in the case where the image captured through photographing includes no spark at such a portion, the assembly 100 is anomalous. Namely, the tester may determine that the ceramic insulator 10 has a through hole.

B6. Modification 6:

The structure of the spark plug production device 500 in the above-described embodiment is merely an example and may be changed in various ways. For example, in the embodiment, the forward end accommodation portion 320 of the pressure container 300 is transparent, and its interior is visible. However, like the upper support portion 310, etc., the forward end accommodation portion 320 may be formed such that its interior is not visible. Similarly, the viewing portion 332 may be formed such that its interior is not visible. Also, the upper support portion 310, the center support portion 330, and the lower support portion 340 may be formed of a transparent material so that the entire chamber 370 is transparent (the interior of the chamber 370 can be viewed from the outside). Also, the spark plug production device 500 may have a structure obtained by vertically inverting the structure in the embodiment. In this case, instead of performing step S125, a base end portion of the assembly 100 is accommodated (inserted) in the insertion hole 290 of the pressing and energizing section 200. Subsequently, the pressing and energizing section 200 accommodating the assembly 100 is moved upward so as to insert the assembly 100 into the chamber 370 of the pressure container 300. Subsequently, step S135 and steps subsequent thereto are performed.

Figure 8:
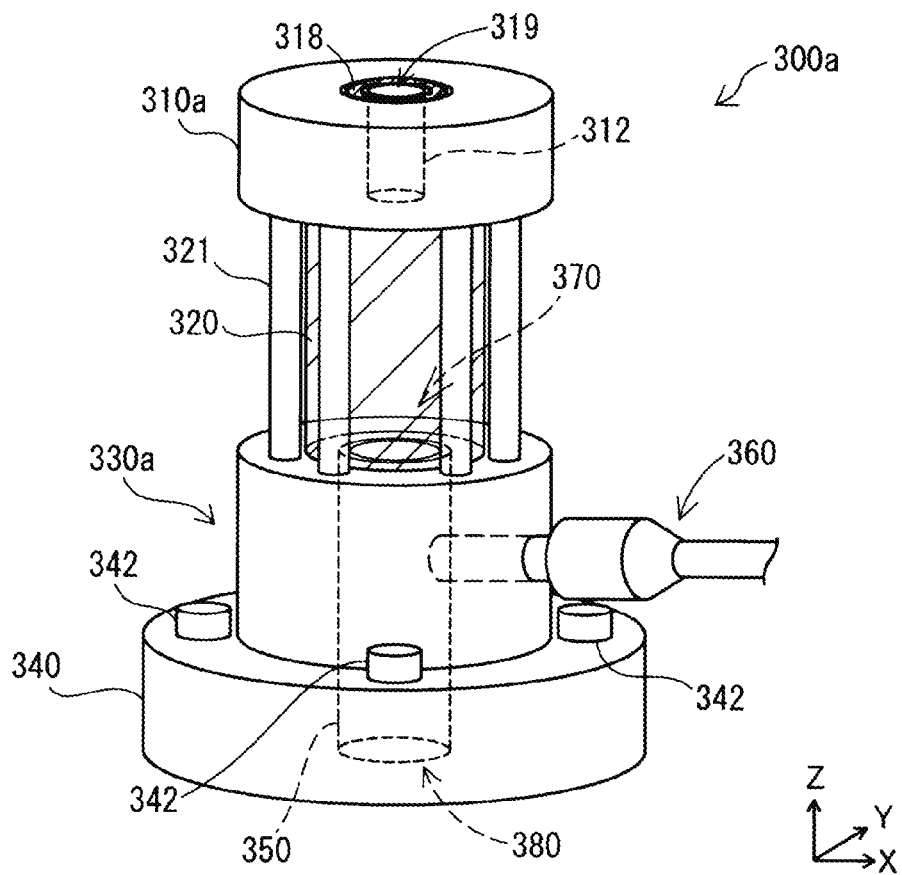
FIG. 8 is a perspective view showing the specific structure of a pressure container 300a according to a modification.

Also, the structure of the pressure container 300 shown in FIG. 4 may be changed as follows. FIG. 8 is a perspective view showing the specific structure of a pressure container 300a in the modification. The pressure container 300a differs from the pressure container 300 of the above-described embodiment in the point that the pressure container 300a includes an upper support portion 310a in place of the upper support portion 310, the point that the seal holder 311 is omitted, the point that the pressure container 300a includes a seal 318 in place of the seal 314, and the point that the pressure container 300a includes a center support portion 330a in place of the center support portion 330. Since other structural elements of the pressure container 300a of the modification are the same as those of the pressure container 300, the same structural elements are denoted by the same symbols and their detailed descriptions are omitted.

The upper support portion 310a differs from the upper support portion 310 of the above-described embodiment in the point that the upper support portion 310a does not have a hole for accommodating the seal 314 and in the point that an annular groove is provided around the opening 319 at the upper end of the accommodation hole 312. Since other structural elements of the upper support portion 310a are the same as those of the upper support portion 310, the same structural elements are denoted by the same symbols and their detailed descriptions are omitted. An annular seal 318 is accommodated in the above-described annular groove provided on the upper end surface of the upper support portion 310a. The seal 318 is formed of a material similar to the material used to form the seal 314 in the above-described embodiment. Notably, in the structure shown in FIG. 8, the opening 319 functions as the opening of the chamber 370 and also functions as the opening of the pressure container 300a.

Figure 9:
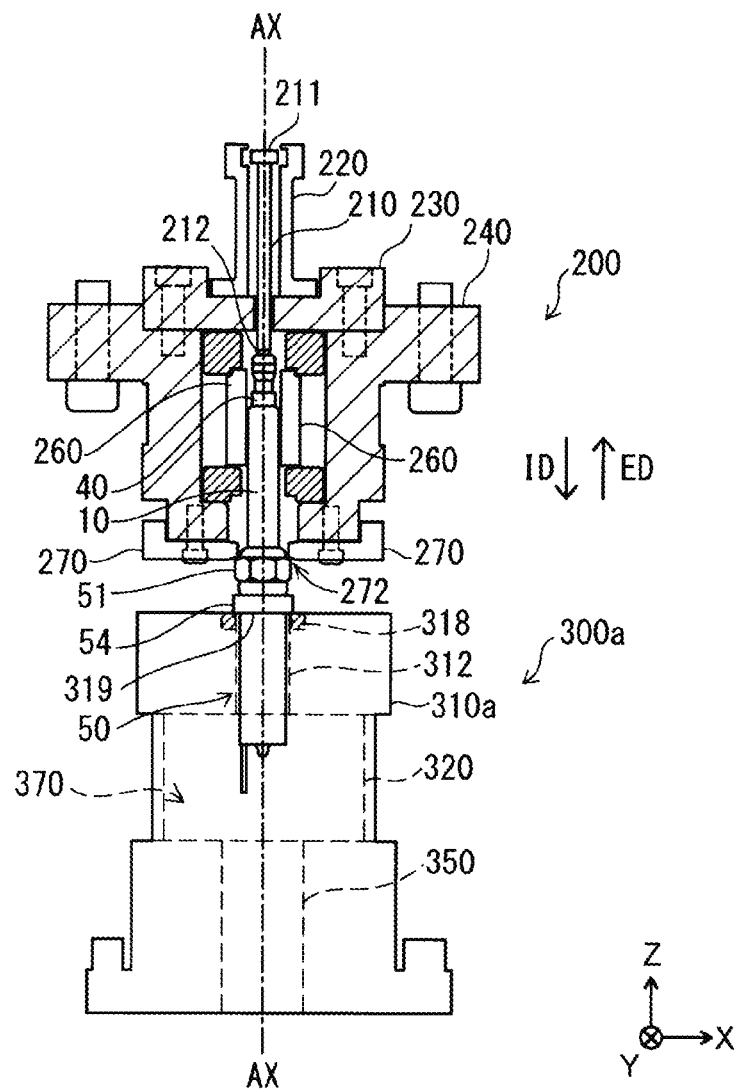
FIG. 9 is an explanatory view showing the states of the spark plug production device of the modification and the assembly 100 during execution of step S130.

FIG. 9 is an explanatory view showing the states of the spark plug production device of the modification and the assembly 100 during execution of step S130. In the modification as well, as in the case of the above-described embodiment shown in FIG. 6, step S130 is performed in a state in which the axial line of the opening of the pressure container 300a (i.e., the opening 319 of the upper support portion 310a) and the axial line AX of the assembly 100 coincide with each other. In the modification as well, the upper end surface of the seal 318 is pressed in the direction along the axial line AX by the forward end surface 55 of the seal portion 54, whereby the opening 319 which is the opening of the pressure container 300a (the chamber 370) is sealed. Therefore, the gas tightness of the pressure container 300a can be improved as in the case of the above-described embodiment.

The present invention is not limited to the above-described embodiment and modifications, and can be realized in various configurations without departing from the spirit of the invention. For example, in order to solve, partially or entirely, the above-mentioned problems or yield, partially or entirely, the above-mentioned effects, technical features of the embodiment and modifications corresponding to technical features of the modes described in the section "SUM- MARY OF THE INVENTION" can be replaced or combined as appropriate. Also, the technical feature(s) may be eliminated as appropriate unless the present specification mentions that the technical feature(s) is essential.

DESCRIPTION OF SYMBOLS

3: ceramic resistor
4a, 4b: seal
6, 7: ring member
8: sheet packing
9: talc
10: ceramic insulator
12: axial hole
13: leg portion
15: insulator step portion
17: forward end side trunk portion
18: base end side trunk portion
19: center trunk portion
20: center electrode
24: second fixing screw
30: ground electrode
31: gap
40: metallic terminal
50: metallic shell
51: tool engagement portion
52: attachment screw portion
53: crimp portion
54: seal portion
55: forward end surface
56: shell internal step portion
57: forward end surface
58: compressively deformable portion
100: assembly
200: pressing and energizing section
210: electrically conductive pin
211: flange portion
212: conductive pin forward end portion
220: guide portion
230: first support portion
232: first fixing screw
240: second support portion
242: second fixing screw
252: upper attachment portion
254: lower attachment portion
260: gripping portion
261: axial hole
270: electrode member
272: edge
274: electrode fixing screw
290: insertion hole
300: pressure container
310, 310a: upper support portion
311: seal holder
312: accommodation hole
313: through hole
314: seal
315: screw accommodation hole
316: fixing screw
318: seal
319: opening
320: forward end accommodation portion
321: supporting column
330: center support portion
331: main support portion
332: viewing portion
333: communication hole
340: lower support portion
342: fixing screw
350: center hole
360: pipe
370: chamber
380: bottom portion
400: voltage application section
405: conductive pin drive section
410: lower fixed plate
412: through hole
420: upper fixed plate
430: supporting column
440: slide support
450: moving shelf
500: spark plug production device
AX: axial line
ID: insertion direction
ED: ejection direction Having described the invention, the following is claimed:

1. A spark plug production device for producing a spark plug which includes an assembly which is composed of a tubular metallic shell having a ground electrode at its forward end and an insulator having an axial hole and holding a terminal electrode in the axial hole such that a portion of the terminal electrode on its base end side is exposed from the axial hole, the assembly being assembled such that the metallic shell covers an outer circumferential surface of a forward end portion of the insulator, the spark plug production device comprising:
a pressure container which has an opening and into which a portion of the assembly on its forward end side is inserted through the opening;
a sealing section which brings an insulating member into contact with an outer circumferential surface of a base end portion of the terminal electrode over the entire circumference of the base end portion in a state in which an axial line of the assembly and an axial line of the opening coincide with each other, and presses the assembly so as to close the opening by the assembly;
a pressurizing section which pressurizes an interior of the pressure container; and
a voltage application section which applies a predetermined voltage between the terminal electrode and the metallic shell,
wherein the pressure container accommodates the portion of the assembly on its forward end side such that a gap formed between an outer circumferential surface of the insulator and an inner circumferential surface of the metallic shell on the forward end side of the assembly is disposed in the pressure container.

2. The device according to claim 1, wherein the sealing section is configured to bring the assembly into close contact with the pressure container in a direction of the axial line of the assembly.

3. The device according to claim 1, wherein the pressurizing section comprises an electrically conductive pin, the electrically conductive pin being configured to come into contact with the base end portion of the terminal electrode and apply the predetermined voltage thereto.

4. The device according to claim 3, wherein the pressurizing section is configured to press the metallic shell, along the axial line of the assembly, in a direction from a base end of the assembly toward a forward end of the assembly to close the opening by the assembly.

5. The device according to claim 3, wherein the pressurizing section is further configured to displace at least one of the electrically conductive pin and the insulating member such that the insulating member relatively moves, along the axial line of the assembly, in relation to the insulator in a direction from the forward end of the assembly toward the base end of the assembly.

6. The device according to claim 5, wherein the pressurizing section is further configured to cause the electrically conductive pin to press the terminal electrode, along the axial line of the assembly, in the direction from the base end of the assembly toward the forward end of the assembly, and wherein the pressurizing section is further configured to displace the insulating member, along the axial line of the assembly, in the direction from the forward end of the assembly toward the base end of the assembly.

7. The device according to claim 1, wherein the pressurizing section is further configured to fit the insulating member onto the terminal electrode from the base end side of the terminal electrode, and wherein the pressurizing section is further configured to press the insulating member, along the axial line of the assembly, toward the forward end side of the assembly, to thereby bring the insulating member into close contact with at least one of an outer circumferential surface of the terminal electrode and an outer circumferential surface of a base end side of the insulator.

* * * * *